(12) United States Patent
Schwenoha

(10) Patent No.: US 6,273,718 B1
(45) Date of Patent: Aug. 14, 2001

(54) DENTAL HANDPIECE

(75) Inventor: Martin Schwenoha, Pantaleon (AT)

(73) Assignee: M & H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 09/564,332

(22) Filed: May 3, 2000

(30) Foreign Application Priority Data

May 5, 1999 (AT) .......................................... 801/99

(51) Int. Cl.$^7$ ...................................................... A61C 1/05
(52) U.S. Cl. ............................................. 433/132; 433/127
(58) Field of Search ................................. 433/132, 127, 433/129

(56) References Cited

U.S. PATENT DOCUMENTS 3,548,501 * 12/1970 Hoffmeister ........................ 433/132
5,807,108 * 9/1998 Schwenoha et al. ................ 433/132

* cited by examiner

Primary Examiner—John J. Wilson
(74) Attorney, Agent, or Firm—Friedrich Kueffner

(57) ABSTRACT

A dental handpiece has a head housing having a turbine chamber and an annular channel. First and second bearings are provided on opposite sides of the turbine chamber in the head housing. An air-driven turbine rotor is arranged in the turbine chamber and supported on the first and second bearings. A rotor spindle is driven by the air-driven turbine and drives, in turn, a tool. The first bearing is positioned proximal to the tool and the second bearing is positioned distal to the tool. The head housing has a drive air channel guiding drive air to the air-driven turbine rotor and a return channel for the drive air. A hollow space is provided in the head housing in which an actuator for the tool holder of the tool is arranged. Several air-permeable connecting channels connect a radially outer area of the turbine chamber to the hollow space or the annular channel or both.

5 Claims, 4 Drawing Sheets

DENTAL HANDPIECE

BACKGROUND OF THE INVENTION

1. Field of the Invention

The invention relates to a dental handpiece with a turbine rotor positioned in the head of the handpiece and driving in rotation the rotor spindle and thus also a tool. The turbine rotor is supported on a side of the rotor facing away from the tool and on a side facing the tool, preferably in roller bearings. The handpiece has a drive air channel for the drive air of the turbine and a return channel for the expanded return air of the turbine.

2. Description of the Related Art

Such handpieces have been known for a long time and have been successfully used in practice.

However, a system-inherent disadvantage of such handpieces is that upon ending a work process in the mouth of a patient, when the drive air is interrupted by actuating a corresponding valve in the handpiece control, the turbine will continue to run because of its inertia. This creates an overpressure at the external side of the turbine rotor and a vacuum in the vicinity of its axis.

Since the channel for the return air opens into the turbine chamber in the external area of the rotor, the air is conveyed by the coasting rotor into the return channel, and in the vicinity of the axis air is sucked in through all of the fine channels and gaps within the handpiece. This means that especially air that is contaminated with saliva and blood of the patient currently being treated is sucked into the handpiece and can penetrate through the bearings into the turbine chamber and into the return air channel.

When the handpiece is again switched on, the air that remained in the area of the turbine chamber and the bearings and contaminants that have settled there are now not only removed through the return air channel by the overpressure generated in the entire turbine chamber but a certain amount is also expelled or blown out to the exterior of the handpiece into the mouth, the saliva, and possibly also into an already open wound of the next patient to be treated.

A solution to this problem is disclosed in patent document AT 403 882 B. In this document it is suggested to provide an axial connection between the turbine and the end of the tool holder facing the tool between an area close to the axis and the return channel so that the turbine, which is coasting after being turned off, moves the air in the way of a flow-technological short-circuit within the head of the handpiece but does not suck in air.

In a variant it is suggested to provide a connecting channel at the side of the rotor facing away from the tool between the return air channel and an opening in the vicinity of the axis of the turbine chamber and/or a hollow space in the area of the actuating element for the tool holder.

When designing a practical embodiment of this variant, one is faced with the problem that because of the miniaturization of the head of the handpiece there is no room or only minimal room available for such a connecting channel.

SUMMARY OF THE INVENTION

It is an object of the present invention to avoid this problem and to provide a head of the handpiece which will not suck in air from the ambient even in the area facing away from the tool during the coasting period of the turbine.

In accordance with the present invention, this is achieved in that the radially outer area of the turbine chamber is connected by at least one air-permeable connecting channel with the hollow space present below the actuating element for the tool holder and/or with an annular channel in the vicinity of the axis, for example, provided between the rotor spindle and head housing.

The objects are solved thus according to the invention in that the radially outer area of the turbine chamber is connected by at least one air-permeable connecting channel with the hollow space located below the actuating element for the tool holder. This connecting channel is, for example, provided in the bearing support and is thus short and linear.

According to the inventive solution, during the coasting period of the turbine the air, present within the outer turbine chamber area and being under overpressure because of the coasting rotor, is conveyed in the area facing away from the tool into the hollow space underneath the push button and from there conveyed through the bearings back into the turbine chamber into the vicinity of the axis where vacuum is present.

It is possible that minimal amounts of air flow can escape to the exterior through fine, tolerance-related gaps and intermediate spaces between the push button and the actual head of the hand piece so that, in any case, any sucking in of ambient air into the handpiece is reliably prevented.

DESCRIPTION OF THE PREFERRED EMBODIMENTS

Figure 1:
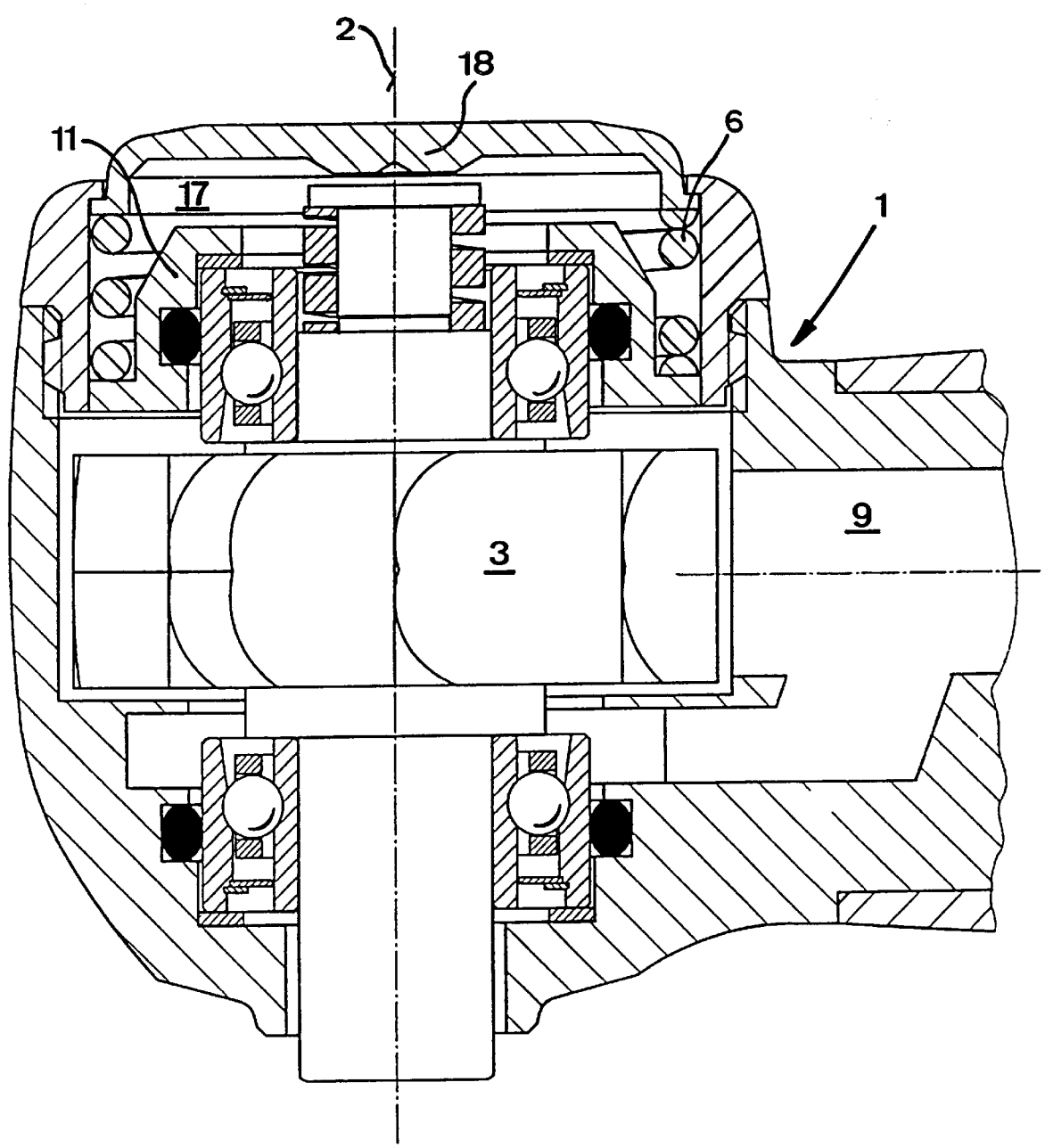
FIG. 1 is an illustration of one of the prior art solutions for a dental handpiece.
Figure 2:
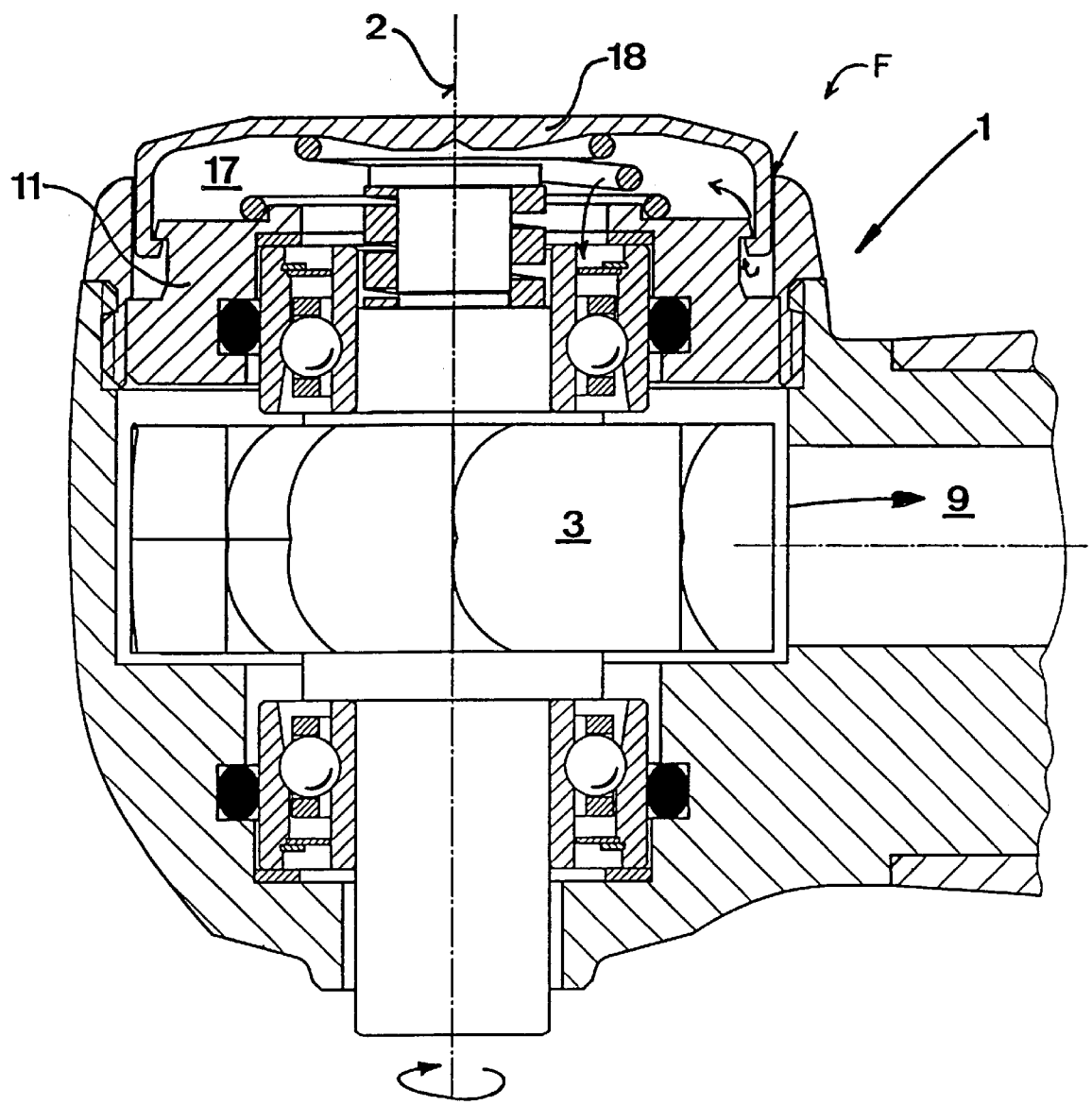
FIG. 2 illustrates the air flow in the upper area of the head of the handpiece without the solution shown in FIG. 1, thus also showing a prior art device.

When comparing the Figures of the drawing, it can be directly seen that the solution according to the invention can be employed for the handpiece according to patent document AT 403 882 B, as shown in FIG. 1, as well as in handpieces discussed in this prior art document and corresponding to the device illustrated in FIG. 2.

As can be seen in FIGS. 1 and 2, the problem of sucking in contaminated air is either not solved at all (FIG. 2) or solved only partially (FIG. 1) in the dental handpieces according to the prior art.

In FIG. 2, arrows F show the path of the ambient air through the annular gap between the push button 18 and the handpiece 1 into the interior of the head of the handpiece and from there through the pushbutton spring into the axially inner area of the turbine housing.

FIG. 1 as well as FIG. 2 illustrate the problems that one is faced with when trying to provide a connecting channel between the return air channel 9 and the hollow space 17 under the push button 18. According to the invention, these problems are satisfactorily solved when at least one connecting channel 12 extends from an axis-remote area of the turbine chamber 10 into the hollow space 17.

Figure 3:
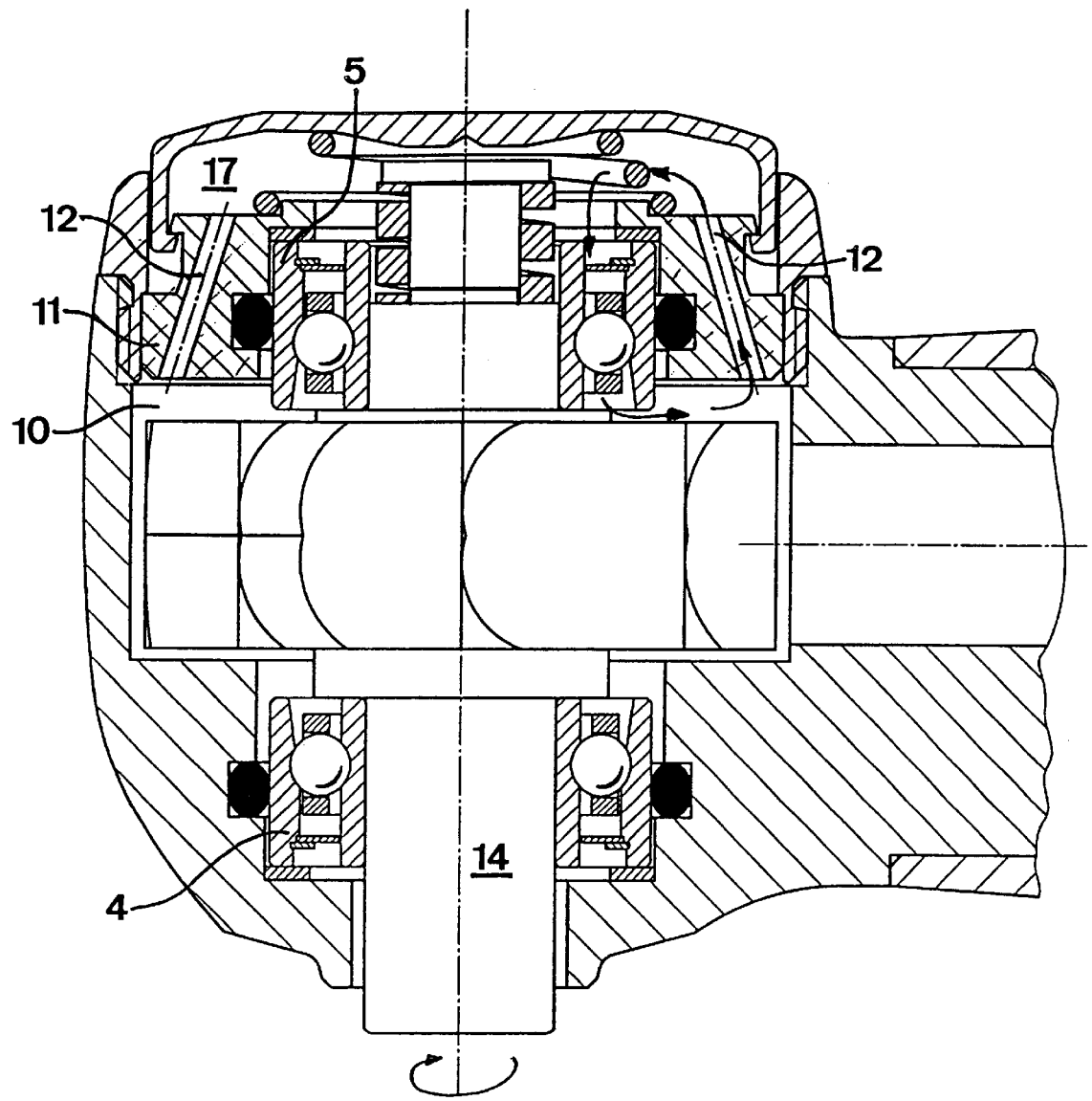
FIG. 3 shows a head of the handpiece similar to that of FIG. 2 with connecting channels according to the invention.

Such a connecting channel 12 can be provided, for example, in the bearing support 11 for the bearing 5 facing away from the tool (see FIG. 3). Even in a design of this support as shown in FIG. 1, a small modification, for example, of the support of the spring 6, makes it possible to provide such a connection without problems.

Figure 4:
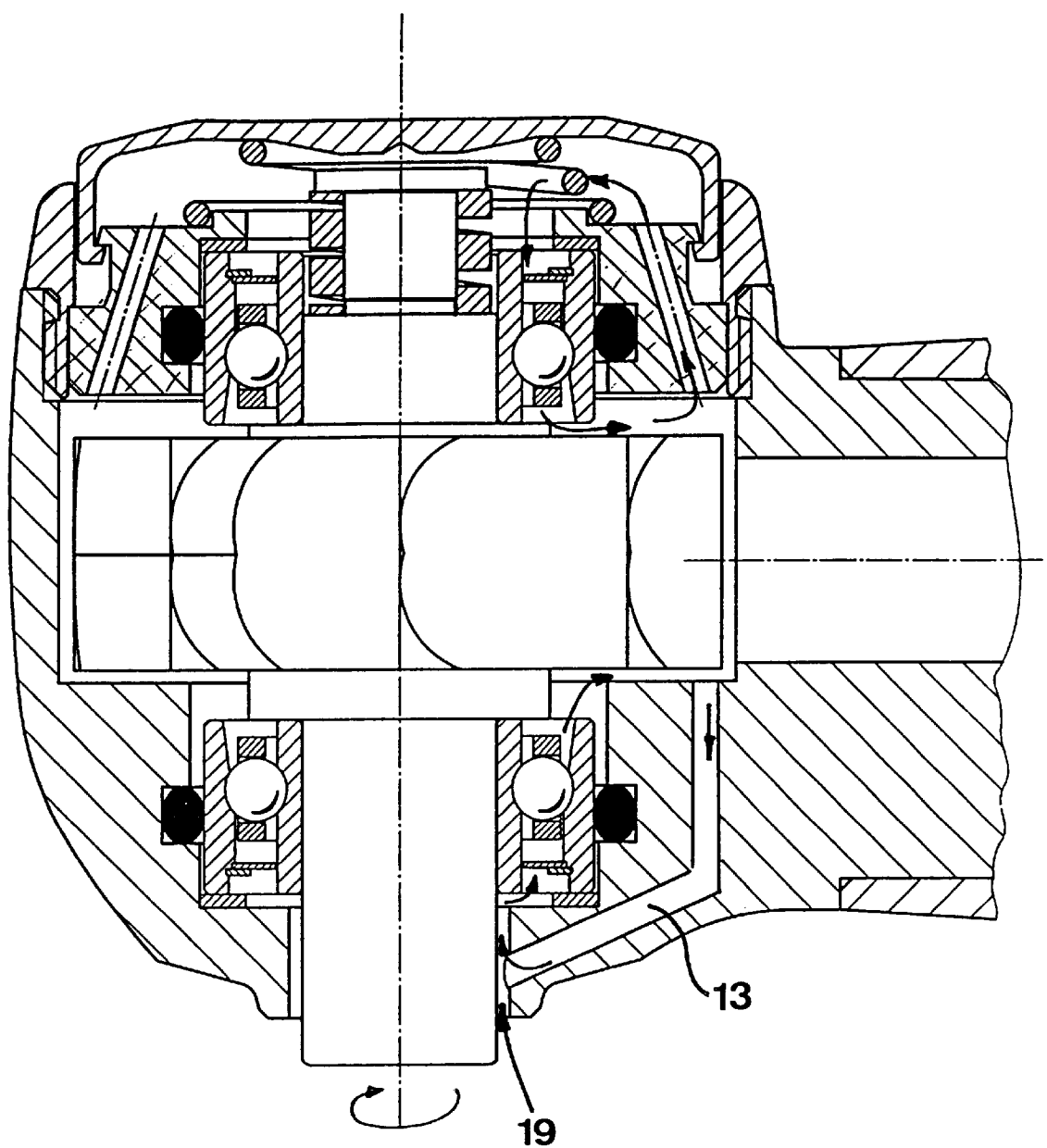
FIG. 4 shows a variant according to the invention with connecting channels on both sides of the rotor.

FIG. 4 shows that the basic idea of the invention can also be applied to the axial area of the rotor facing the tool. The angled connecting channel 13 connects the radially outer area of the turbine chamber 10 with the annular gap between the rotor spindle 14 and the wall of the head housing.

FIG. 4 also shows channels 12 in analogy to FIG. 3. Thus, the solution according to the invention can be provided at both sides of the rotor.

While specific embodiments of the invention have been shown and described in detail to illustrate the inventive principles, it will be understood that the invention may be embodied otherwise without departing from such principles.

What is claimed is:

1. A dental handpiece comprising:

a head housing having a turbine chamber and an annular channel;

the head housing having a first bearing and a second bearing on opposite sides of the turbine chamber;

an air-driven turbine rotor arranged in the turbine chamber and supported on the first and second bearings;

a rotor spindle in driving connection with the air-driven turbine and configured to drive a tool, wherein the annular channel is formed between the rotor spindle and a wall of the head housing;

the first bearing positioned proximal to the tool and the second bearing positioned distal to the tool;

the head housing having a drive air channel configured to guide drive air to the air-driven turbine rotor;

the head housing having a return channel for the drive air;

the head housing having a hollow space in which an actuator for a tool holder of the tool is arranged;

one or more air-permeable connecting channels configured to connect a radially outer area of the turbine chamber to at least one of the hollow space and the annular channel, wherein each of the one or more air-permeable connecting channels has an end opening into the least one of the hollow space and the annular channel, and wherein each end is located axially outwardly from the first and second bearings.

2. The dental handpiece according to claim 1, wherein the first and second bearings are roller bearings.

3. A dental handpiece comprising:

a head housing having a turbine chamber and an annular channel;

the had housing having a first bearing and a second bearing on apposite sides of the turbine chamber;

an air-driven turbine rotor arranged in the turbine chamber and supported on the first and second bearings;

a rotor spindle in driving connection with the air-driven turbine and configured to drive a tool, wherein the annular channel is formed between the rotor spindle and a wall of the head housing;

the first bearing positioned proximal to the tool and the second bearing positioned distal to the tool;

the head housing having a drive air channel configured to guide drive air to the air-driven turbine rotor;

the head housing having a return channel for the drive air;

the head housing having a hollow space in which an actuator for a tool holder of the tool is arranged;

a plurality of air-permeable connecting channels configured to connect a radially outer area of the turbine chamber to at least one of the hollow space and the annular channel, wherein several of the air-permeable connecting channels are arranged in a bearing support of the second bearing at a slant to a bearing axis of the second bearing and are distributed circumferentially.

4. The dental handpiece according to claim 3, wherein several of the air-permeable connecting channels are arranged in the head housing and circumferentially distributed about the first bearing, wherein the air-permeable connecting channels are angled.

5. A dental handpiece comprising:

a head housing having a turbine chamber and an annular channel;

the head housing having a first bearing and a second bearing on opposite sides of the turbine chamber;

an air-driven turbine rotor arranged in the turbine chamber and supported on the first and second bearings;

a rotor spindle in driving connection with the air-driven turbine and configured to drive a tool. wherein the annular channel is formed between the rotor spindle and a wall of the head housing;

the first bearing positioned proximal to the tool and the second bearing positioned distal to the tool;

the head housing having a drive air channel configured to guide drive air to the air-driven turbine rotor;

the head housing having a return channel for the drive air;

the head housing having a hollow space in which an actuator for a tool holder of the tool is arranged;

a plurality of air-permeable connecting channels configured to connect a radially outer area of the turbine chamber to at least one of the hollow space and the annular channel, wherein several of the air-permeable connecting channels are arranged in the head housing and circumferentially distributed about the first bearing, wherein the air-permeable connecting channels are angled.

\* \* \* \* \*

UNITED STATES PATENT AND TRADEMARK OFFICE
CERTIFICATE OF CORRECTION

PATENT NO. : 6,273,718 B1
DATED : August 14, 2001
INVENTOR(S) : Martin Schwenoha It is certified that error appears in the above-identified patent and that said Letters Patent is hereby corrected as shown below:

<u>Title page,</u>
Assignee should read:
-- [73] Assignee: W & H Dentalwerk Bürmoos GmbH, Bürmoos (AT) --

Signed and Sealed this

Fourth Day of June, 2002

*Attest:*

*Attesting Officer*

JAMES E. ROGAN
*Director of the United States Patent and Trademark Office*